United States Patent [19]
Schwender et al.

[11] 4,012,387
[45] Mar. 15, 1977

[54] BENZO-[g]PYRIDO[2,1-b] QUINAZOLINONES

[75] Inventors: Charles F. Schwender, Lebanon; Brooks R. Sunday, Hackettstown, both of N.J.

[73] Assignee: Warner-Lambert Company, Morris Plains, N.J.

[22] Filed: Sept. 18, 1975

[21] Appl. No.: 614,399

[52] U.S. Cl. .................. 260/251 A; 260/256.4 F; 260/256.5 R; 424/251
[51] Int. Cl.² ................................. C07D 471/04
[58] Field of Search ............. 260/251 A, 256.4 F, 260/256.5 R; 424/251

[56] References Cited
FOREIGN PATENTS OR APPLICATIONS 2,513,930  10/1975  Germany

OTHER PUBLICATIONS

Seide, Chemical Abstracts, vol. 19, 1282 (1925).
Zeide et al., Chemical Abstracts, vol. 32, 572²(1938).
Zeide et al., Chemical Abstracts, vol. 32, 572³(1938).
Halleux et al., J. Chem. Soc. (C) pp. 881–887 (1970).
Beilstein, Zweites Ergaenzungswerk, EII 25, p. 238 (1954).

*Primary Examiner*—Donald G. Daus
*Assistant Examiner*—Diana G. Rivers
*Attorney, Agent, or Firm*—Albert H. Graddis; Frank S. Chow; George M. Yahwak

[57] ABSTRACT

This invention relates to novel benzo- and tetrahydrobenzo-[f,g and h]pyrido[2,1-b]quinazolin-ones and their methods of preparation. These compounds have utility as antiallergy agents.

2 Claims, No Drawings

BENZO-[g]PYRIDO[2,1-b] QUINAZOLINONES

The present invention relates to compounds of the following generic series:

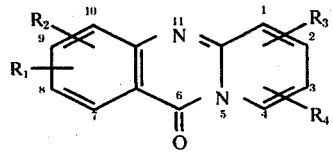

where $R_1$ and $R_2$ together represent CH=CH—CH=CH as a fused benzo moiety or —$(CH_2)_4$—as a fused tetrahydrobenzo moiety at positions 7,8 or 8,9 or 9,10 of the ring system. In addition the benzo- and tetrahydrobenzo-quinazolinone portion may be optionally substituted by hydrogen, halogen, alkoxy, cyano, alkyl, alkenyl, aminoalkoxy, hydroxyalkoxy, hydroxy, aralkyloxy, trifluoromethyl, nitro, amino, monoalkylamino, dialkylamino, aralkylamino, acylamino, sulfonyl, amino, carboxy, carboalkoxy, carboxamido or N-substituted carboxamido, methylsulfinyl, methylsulfonyl, phenylsulfinyl, phenylsulfonyl, substituted phenylsulfonyl, sulfonamido, sulfonic acid, acrylic acid, oxyacetic acid, tetrazoyl, N-(tetrazolyl)-carboxamido and tetrazolylethylene or mixture thereof. $R_3$ is selected from a group consisting of hydrogen, alkyl, hydroxyl and alkoxy. $R_4$ is selected from a group consisting of hydrogen, hydroxy, hydroxyalkyl, hydroxyalkoxy, carboxy, carboalkoxy, carboxamido and N-substitited carboxamido, tetrazolyl, N-tetrazolylcarboxamido, tetrazolylethylene, cyano, sulfonamido and sulfonic acid, acrylic acid, oxyacetic acid and oxymethyltetrazolyl optionally appearing at positions 1–4 of the pyrido ring.

The preferred compounds are those structural species which contain at least one acidic function substitution either at $R_4$ and/or the benzo- or tetrahydrobenzoquinazolinone portion. These are preferably carboxyl, sulfonic acids and tetrazolyl, cyano, or their esters or pharmaceutically acceptable salts. That is, if the benzo- or tetrahydrobenzoquinazolinone portion contains an acid group tetrazolyl, cyano, or ester, then $R_4$ may be as indicated above. If $R_4$ is an acidic group tetrazolyl, cyano, or ester, then the benzo- or tetrahydrobenzoquinazolinone portion may be substituted as indicated above. In addition, $R_4$ and the benzo- or tetrahydrobenzoquinazolinone substitution may both be acidic groups tetrazolyl, cyano, or their esters.

As used above, the term halogen refers to chlorine, bromine, and flourine; alkoxy refers to radicals wherein the alkyl moiety contains one to eight carbon atoms, preferably 1 to 6 in straight or branched chains or as cyclic 4,5 carbons; alkyl refers to radicals containing one to eight carbon atoms, preferably 1 to 6 carbons in straight or branched chains or as cyclic 5 or 6 carbons; alkenyl refers to radicals of 1 to 6 carbons; aralkyl refers to benzyl, phenylethyl, and phenylpropyl radicals; aralkyloxy refers to the structures as defined for aralkyl; acyl relates to those radicals which are derived from alkanoic acids of 1 to 6 carbons, or aroyls such as benzoyl.

The preferred compounds of this invention include:

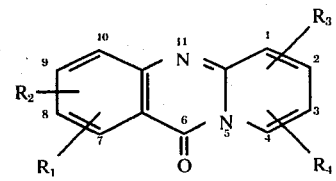

where:

1. $R_1R_2$ = 8,9-benzo, $R_3$ = H, $R_4$ = 3-COOH
2. $R_1R_2$ = 8,9-dibenzo, $R_3$ = H, $R_4$ = 1-COOH
3. $R_1R_2$ = 8,9-benzo, $R_3$ = H, $R_4$ = 2-COOH
4. $R_1R_2$ = 7,8-benzo, $R_3$ = H, $R_4$ = 3-COOH
5. $R_1 R_2$ = 7,8-benzo, $R_3$ = H, $R_4$ = 2-COOH
6. $R_1R_2$ = 7,8tetrahydrobenzo, $R_3$ = H, $R_4$ = 3-COOH
7. $R_1 R_2$ = 7,8-tetrahydrobenzo, $R_3$ = H, $R_4$ = 2-COOH
8. $R_1 R_2$ = 8,9benzo, $R_3$ = H, $R_4$ = 3-(tetrazolyl)
9. $R_1 R_2$ = 8,9-benzo, $R_3$ = H, $R_4$ = 2-(tetrazolyl)
10. $R_1R_2$ = 7,8-benzo, $R_3$ = H, $R_4$ = 3-(tetrazolyl)
11. $R_1R_2$ = 7,8-benzo, $R_3$ = H, $R_4$ = 3-(tetrazolyl)
12. $R_1R_2$ = 7,8-tetrahydrobenzo, $R_3$ = H, $R_4$ = 3-(tetrazolyl)
13. $R_1R_2$ = 7,8-tetrahydrobenzo, $R_3$ = H, $R_4$ = 2-(tetrazolyl)

The compounds of this invention may be prepared by three chemical. routes:

At this time, three processes yield the compounds of this invention.

1. A fusion of the appropriately substituted-anthranilate ester with 1-1.25 equivalents of 2-chloropyridine-3,4,5- or 6-carboxylic acid and 0.05–1.1 equivalents of potassium iodide at 100°–250° for 0.25–3 hours gives the crude product as a solid upon cooling. Purification is achieved by recrystallization or by washing the crude solid with a hot alcohol.

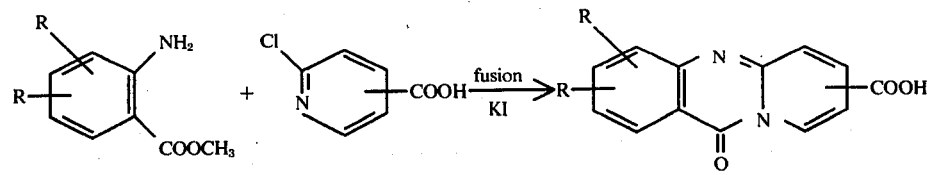

2. The appropriately substituted-anthranilic acid is heated at reflux for 2–72 hours with 1–2 equivalents of the appropriate 2-chloropyridine in 5–20 parts glacial acetic acid or similar alkanoic acid. The expected product is obtained as a precipitate by cooling or by pouring the reaction mixture upon ice. The crude product is purified by recrystallization from pyridine or by washing with a hot alcohol such as ethanol.

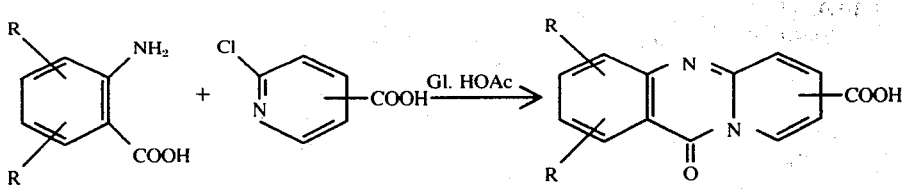

3. The desired products may also be obtained by heating, at reflux temperature, 65°–140°, a mixture of the appropriately substituted-anthranilic acid and 1–2 equivalents of 2-chloropyridine-3,4,5- or 6-carboxylic acid in 5–50 parts of an alcohol containing 0.1–1.1 equivalents of hydrochloric acid. The crude product is obtained as a precipitate from the reaction mixture and is purified by recrystallization from pyridine or by washing with a hot alcohol such as ethanol.

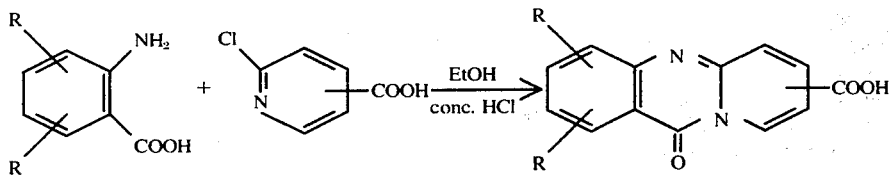

Furthermore, the chloronicotinic acids may be replaced in these reactions by the following pyridine analogs and any such combinations of $R_1$ and $R_2$.

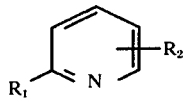

| $R_1$ | $R_2$ |
|---|---|
| 2-Cl | 3,4,5- or 6-CONH$_2$ |
| 2-OH | 3,4,5- or 6-CN |
| 2-SCH$_3$ | 3,4,5- or 6-alkyl (1–8 c's) |
| 2-OCH$_3$ | 3,4,5- or 6-alkoxy (1–8 c's) |

The following examples are given to more specifically define the method of making the compounds of the formula:

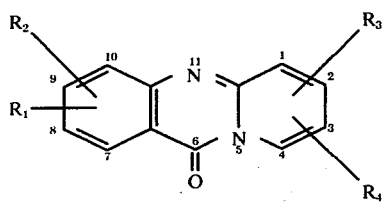

| Ex. | $R_1$ $R_2$ | $R_3$ | $R_4$ | mp | Anal. | Route Prep. |
|---|---|---|---|---|---|---|
| 1 | 8,9-benzo | 3-COOH | H | 375–84° dec. | CHN | No. 2 |
| 2 | 8,9-benzo | 1-COOH | H | 284–85° dec. | CHNCl | No. 3 |

EXAMPLE 1

6-oxo-6H-benzo[g]pyrido[2,1-b]quinazoline-3-carboxylic acid

A reaction mixture containing 68.0g (364 mmol) of 3-amino-2-naphthoic acid, 57.4g (364 mmol) of 6-chloronicotinic acid and 900ml of glacial acetic acid was heated at reflux temperature for 16 hours. The reaction mixture was cooled at 25° and the resultant precipitate was collected to give 70.0g, mp. 270°–282° dec of a yellow solid. The crude product was recrystallized twice from pyridine to give the yellow crystalline product, mp. 375°–384° dec.

Anal. Calcd. for $C_{17}H_{10}N_2O_3$: C, 70.34; H, 9.65. Found: C, 70.10; H, 3.48; N, 9.52.

EXAMPLE 2

6-oxo-6H-benzo[g]pyrido[2,1-b]quinazoline-1-carboxylic acid

An ethanolic mixture (180ml) containing 5.00g (26.8 mmol) of 3-amino-2-naphthoic acid, 4.21g (26.8 mmol) of 2-chloronicotinic acid and 2.1ml. of conc. HCl was heated at reflux for 72 hours. The resultant suspension was cooled and yielded an orange-red powder upon filtration; yield 3.1g (40%), mp. 285°–88° dec. Recrystallization from DMF gave the analytical sample; 2.21g, mp. 283.5°–285° dec.

Anal. Calcd. for $C_{17}H_{10}N_2O_3$: C, 70.34; H, 3.47; N, 9.65. Found: C, 70.17; H, 3.59; N, 9.49.

Compounds of this invention have been found to reduce allergic responses to antigen challenge by inhibiting antibody-antigen reactions in mammals such as rats, when tested in accordance with the procedure of Herzig [*Immunopharmacology*, M. E. Rosenthale and H. C. Mansmann, Eds., John Wiley and Son, N.Y., 1975]. Following this protocol, the table below shows comparative data between the effectiveness of the compound according to Example 1 an Intal (Cromoglycate) which is presently the commercial compound of choice for use in allergic bronchial asthma.

TABLE 1

Effective dose 50% inhibition rat passive cutaneous anaphylaxis test (ED$_{50}$-PCA)

| | | ED$_{50}$-PCA (rat) | |
|---|---|---|---|
| | ip. | iv. | po. |
| Example 1 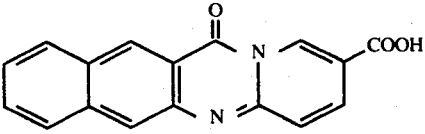 | 0.015mg/kg | 0.015mg/kg | <0.1mg/kg |
| Intal 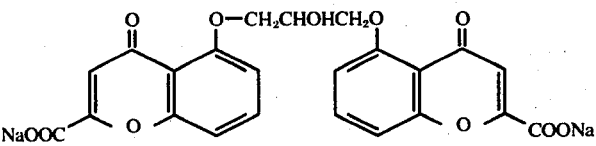 | inactive | 1–2mg/kg | inactive |

As can be seen, the Example 1 compound is active when given orally or intraperitonially whereas the commercial compound is not. Furthermore, when compared for i.v. administration, the novel compound is many times as effective as the commercial compound.

These compounds may be administered orally, parenterally or by aerosol at a dose of 0.005–20mg/kg. Compounds of this invention are useful in the management of allergic reactions such as bronchial asthma.

We claim:
1. 6-oxo-6H-benzo[g]pyrido[2,1-b]quinazoline-3-carboxylic acid.
2. 6-oxo-6H-benzo[g]pyrido[2,1-b]quinazoline-1-carboxylic acid.

* * * * *